(12) United States Patent
Gant

(10) Patent No.: US 6,371,133 B1
(45) Date of Patent: *Apr. 16, 2002

(54) VARIABLE-GUAGE TOOTH-FLOSSING LOOPS

(75) Inventor: Kathleen Gant, Fallbrook, CA (US)

(73) Assignee: Loops, L.L.C., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/640,515

(22) Filed: May 1, 1996

(51) Int. Cl.⁷ ............................................... A61C 15/00
(52) U.S. Cl. ...................................... 132/321; 132/329
(58) Field of Search ................................ 132/321, 329; 24/17 B; 57/21, 201; 433/15

(56) References Cited

U.S. PATENT DOCUMENTS

| | | | |
|---|---|---|---|
| 3,491,776 A | | 1/1970 | Fleming |
| 3,511,249 A | | 5/1970 | Baitz |
| 3,800,812 A | * | 4/1974 | Jaffe ........................... 132/321 |
| 4,265,258 A | | 5/1981 | Eaton |
| 4,315,517 A | | 2/1982 | Krag |
| 4,450,849 A | | 5/1984 | Cerceo |
| 4,523,600 A | | 6/1985 | Donovan |
| 4,550,741 A | | 11/1985 | Krag |
| 4,776,358 A | | 10/1988 | Lorch ........................... 132/321 |
| 4,836,226 A | | 6/1989 | Wolak ........................... 132/321 |
| 4,974,615 A | * | 12/1990 | Doundoulakis ............. 132/321 |
| 4,998,978 A | | 3/1991 | Varum ........................... 132/321 |
| 5,242,175 A | * | 9/1993 | O'Leary ..................... 273/440 |
| 5,378,146 A | * | 1/1995 | Sterrett ......................... 433/15 |
| 5,518,012 A | * | 5/1996 | Dolan et al. ................. 132/321 |
| 5,588,452 A | * | 12/1996 | Peck ........................... 132/321 |

FOREIGN PATENT DOCUMENTS

| | | | | |
|---|---|---|---|---|
| GB | 2128133 | * | 4/1984 | .................. 132/321 |
| WO | 8100959 | * | 4/1981 | .................. 132/321 |
| WO | 92/06648 | * | 4/1992 | .................. 132/323 |

* cited by examiner

*Primary Examiner*—Todd E. Manahan
(74) *Attorney, Agent, or Firm*—Foley & Lardner; Bernard L. Kleinke

(57) ABSTRACT

Embodied in the flexile forms of both an endless-loop and as a linear-tape, a unique tooth flossing device for cleaning away bacteria between the teeth is set forth. Comprised of a nontoxic extrusion-molded thermo-plastic polyurethane having particular properties of excellent elasticity, almost film-like guage of thickness, and a natural random surface-texture serving to aid the flossing procedure. In use, a FLOSS-LOOP™ is simply held in the user's thumb-&-forefinger of both hands, so as to pre-stretch "thin" that portion to be slid vertically between the teeth. The exceptionally high stretched tensile-strength of this device enables it to endure the duress of insertion between the teeth, yet once interposed interstitially adjacent the gum-line, the release of excess tension upon the tensioned segment of the loop enables it to resume it's natural thickness-guage of approximately 0.325 mm(0.0128-inch). This novel variable-guage capability of the device, making it able to more effectively burnish away substances from the tooth and sulcus of the gum-tissue during it's thicker guage modality; then again be retensioned to approximately only 0.200 mm-guage for easy interstitial removal. Either version of the device may be coated with various agents effective in combating diseases of the teeth and gums.

18 Claims, 1 Drawing Sheet

VARIABLE-GUAGE TOOTH-FLOSSING LOOPS

I.) BACKGROUND OF RELEVANT EARLIER INVENTION

This invention specifically relates to dental-floss generally employed for cleaning of plaque bacteria, and dislodging of debris away from: the interproximal regions of the teeth and gums; -and more particularly, it relates to those types of flossing devices embodied in band or in tape configuration, and provision of some form of dentrifice therewith.

Heretofore, there have been a variety of dental-floss materials ranging from early string like embodiments supplied upon a spool, to resinous bands adapted to a handle with bifurcated prong band holders. Accordingly, background research discovery provides some prior patent-art regarded as germane to this disclosure.

Chronologically for example U.S. Pat. No. 3,491,776 (filed: June, 1967 to Floxite Co.) shows a "dental cleaner for removal of tobacco and other stains from teeth", embodied as a narrow inelastic strip of paper material having a thin wax-coating into which is imbedded abrasive particles. The abrasive is thus able to somewhat move along the surface of the strip during the tooth cleaning procedure.

In U.S. Pat. No. 3,511,249(filed: May, 1968 from Australia) shows a "device for dislodging food-particles from between human-teeth", embodied as a narrow rubber-band like strip having sinuously undulated opposed edges, which irregularities serve to exert a cleaning action when the device is stretched to fit between the teeth in a reciprocal manner.

In U.S. Pat. No. 3,800,812(filed: November, 1972 to Pauldan-Indus.,Inc.) sets forth an extruded 1.5–10 mill gauge polyester-elastomer tape which is said to be post-stretched to increase it's resilience; and, may include flavoring and agrasive-particles in the resin or applied after extruced. However, the polymer actually lacks sufficient tinsel-strength for needed durability.

In U.S. Pat. No. 4,265,258(filed: August, 1979) shows an inelastic "dental-floss" having a relatively large compressible diameter in order to provide an increased surface-area, and may be comprised of from one to three twisted strands of dental-floss; in all examples the floss presenting a multitude of random fiberous-hair like extensions therefrom.

In U.S. Pat. No. 4,315,517(filed: October, 1978) shows a "device for cleaning teeth to prevent formation of plaque", which is a length of string like dental-floss material. It's inventor teaches various methods of connecting the opposite-ends together, in order to provide a continuous-loop in which at least two fingers may be admitted while manually manipulating the device between one's teeth.

In PCT/US80/01293(orig.filed: October, 1979) is shown another type of flosing loop made of a woven-fiberous polymide ribbon material which is formed into a series of chain-like interconnected loops, whereby a loop portion is drawn from a spool-dispenser having an integral cutting-blade enabling a single loop to be readily detatched from the spool-dispenser.

In U.S. Pat. No. 4,450,849(filed: September, 1982) shows a "dental physio-tape" which is a 1 mm–10 mm wide polymer material having obliquely zig-zaging rows of tiny embossed protuberances upon both sides of the tape. The 1.5–3 mill-thickness tape can have antiseptic and antibiotic properties, by including within the tape's polymer-resin such solution or plastizer additives said known to the plastic-molding art.

In U.K. Pat. No. 2,128,133(filed: October 1982) is shown an extruded dental-floss tape constituted by a so called incipiently fibrillatable (given perforations to enhance abrasion against tooth-enamel) polyolefine plastic-film such as polypropylene, which is chilled and roller-embosed for surface texture.

In U.S. Pat. No. 4,523,600(filed: July, 1983) shows a "dental flossing product", which is a multifilament flossing-thread trained about the fingers of user's tensioning hands. The disclosure teaches means by which the opposite ends of the thread are tied together to form a continuous loop having two tails where joined; the device thus being trained about the fingers of opposite hands while being manipulated between user's teeth.

In U.S. Pat. No. 4,550,741(filed: February, 1984 to Dental-Preventech Co.) shows a "device for cleaning teeth to prevent formation of plaque", wherein is set forth various methods by which to securely join the ends of dental-floss so as to create a loop 2–4 inches in diameter.

In U.S. Pat. No. 4,776,358(filed: May, 1988) is shown a "floss employing microporous tapes sandwiching paste dentifrice", which entails a manufacturing process for making a strip of porous polymer material containing a liquid dentifrice which migrates out during usage of the strip between one's teeth.

In U.S. Pat. No. 4,817,643(filed: July, 1987 to Oral-B Co., ULTRA-FLOSS®) is shown an elastic "Chinese finger-cuff like dental-floss", wherein minute nylon-fibers are woven in an opposing helice-spiral pattern leaving a hollow-center which may be filled with a dentifrice such as mint-fluoride or a cleaning substance. The floss diameter can be controlled by the longitudinal tension applied to it, thus the floss can be constricted to more easily pass between tightly spaced teeth.

In U.S. Pat. No. 4,836,226(filed: November, 1987) is shown an "endless article for cleaning teeth", which is a loop of elastic material having a circumference of 3–9 inches, and is said preferably ¼-inch wide×⅓₂nd-inch(0.0938-inch) thickness guage, but can have a round cross-section of from ⅓₂nd-inch(0.0938-inch) to ⅛th-inch(0.125-inch) diameter. The surface should be coated with wax or teflon, and is provided with nodules or circumferential-ribs, either of which serving to abrade away debris from the intersections of proximal areas between teeth; and is elastic as to be stretchable for easier placement between the teeth. However while inventor R.G.Wolak of this patent stated that his closest prior-art appeared to be a common rubber-band(or o-ring), and his patent probably represents the most relevant prior-art hereof, it remains that none of the materials (KEVELAR, TEFLON, GIRTEX, Nylon, Polyester, Silicon) claimed for use by Wolak exhibit the necessarily particular attributes of the special polymer material being claimed elsewhere herein by the instant inventor hereof. Moreover, because the materials identified by Wolak do not exhibit the necessary unique combination of modulas-of-elastisity and tensil-strength at the extreme thinness necessary to translate successfully through the frequently very narrow interstitial spaces generally found between abutting teeth; Wolak had thus resorted to provision of a coating of Wax or TEFLON as a way of endeavoring to attain sufficient slipperiness as to facilitate interstitial passage. Owing that the Wolak patent never redeemed itself successfully in the marketplace, it is indeed apparent that the materials involved in his invention did not perform adequately to merit dental-hygienist or public acceptance. The thinnest guage identified by Wolak's materials is said 0.0313-inch(0.7938mm), which is over twice the thickness considered truly workable as a flossing-tape. Hence, Wolak's disclosure was not a truly viable article from a practical standpoint, as it simply did not contemplate the characteristics of a superior polymer material, nor did it anticipate the necessary employment of Polyurethane in particular.

In U.S. Pat. No. 4,974,615(filed: July, 1989) is shown an elastic mono-filament of circular or flat cross-section, and may have a plurality of regularly spaced-apart perforations, spaced-apart transverse-slits, spaced-apart nodules, or spaced-apart knot-like entities; but no specific polymer-material is actually identified or contemplated that would make the device function in the manner prescribed.

In U.S. Pat. No. 5,518,012(filed: June, 1994 to Gore & Assoc.,Inc.) is shown an expanded polytetrafluoroethylene (PTFE) or Teflon® material having a minimum gauge of 50–75 $\mu$m (and a width of 0.5 mm–1.1 mm), which is said to be a single-layer of fibrillation material not folded upon itself like it's PTFE predecessors; and, to exhibit a characteristic permanent thinning extrusion-action as it is pulled through tight spaces between the teeth.

In U.S. Pat. No. 5,588,452(filed: May, 1995) is shown a combination toothpick and reusable flossing device, being a flat (about 0.5 mm–2.25 mm gauge×0.4–0.8 mm width), stiff, yet resilient elongated strip of polyester or nylon plastic material, having a textured surface for abraiding between teeth.

In U.S. Pat. No. 4,998,978(filed: January, 1990) is shown a "tooth cleaning strip", which is a flat flexible member about 1/8-inch wide×4-mills guage thickness. It is constructed of crossed-strands which form cross-ridges at the surface, the cross-ridges thus serving in frictional scrubbing engagement against the teeth.

Therefore, in full consideration of the preceding patent review, there is determined a need for an improved form of device to which these patents have been largely addressed. The instant inventor hereof believes their newly improved dental-floss device commercially referred to as FLOSS-LOOPS™, currently being developed for production under auspices of the LOOPS, LLC (mfg./Mkt.Co.)exhibits certain advantages as shall be revealed in the subsequent portion of this instant disclosure.

II.) SUMMARY OF THE INVENTION

A.) In view of the foregoing discussion about the earlier invention art, it is therefore important to make it pellucid to others interested in the art that the object of this dental-hygiene invention is the notion of employing a novel elastic dental-floss material made of strong flexible, non-tacky, non-toxic, preferably translucent polyurethane polymer resin. The invention is suitable for use by the general public, and is designed for easy manipulation even among geriatrics, as well as children sometimes lacking developed finger dexterity.

It possesses a unique lightly striated or variegated surface texture character, generally distinguished as a random pattern of pits as viewed via a magnifying-glass, but which is even viewable via normal-eye. This intrinsic surfacing characteristic is common to both side-wall surfaces of this dental-floss invention, in the floss-tape embodiment, and in it's floss-loop configuration. The special flossing material is thus generally held taut between thumb and forefinger of both hands, while positioned vertically into the interstitial regions. The floss-material being capable of providing a desirably slight abrading action, sufficient as to effectively burnish away substances from the interstitial regions of the teeth, as well as the sulcus of the supporting gum-tissue during it's lightly-tensioned thicker gauge modality of usage. Alternately, the user can simply exert additional tensioning effort during interstitial ingress/egress of the floss, causing the flat shaped cross-section to readily shrink under tension into an almost film-like thickness, thereby easily slipping past difficult interstitial constrictions.

B.) Another object of this invention disclosure is to set forth a special extrusion-molded (linear-strip or as a continuous-band) flexible polyurethane dental-floss article having general physical properties defined as preferably exhibiting—a nominally relaxed thickness-guage: 0.325 millimeters(0.0128-inch), width: 3/32-inch(loop) to 3/8-inch (tape), specific-gravity: 1.1–1.2, maximum-elongation: 300–400%, modulas-of-elasticity: 70 (about 1/3rd-thickness of rubber to sustain same elasticity), contains no toxic substances such as formalin, sulfer, lead, arsenis, etc., not effected by water, stable heat-resistance from–35° C. to over 80° C., and no significant change in tenacity after expansion to 200%(3× stretch); -plus an exceptionally high tensile-strength, enabling this special dental-floss to endure the duress of repeated insertions between teeth. Note, that while the stated dimensional characteristics of the flossing device are considered most preferable, it remains that thicknesses substantially heavier (to as thick as 0.020-inch/0.50-millimeters), and conversely, thinner can still be employed within the purview of the term "nominal"-thickness.

C.) Another object of this invention disclosure is to set forth a special dental-floss article made of polyurethane, which may be coated (generally sprayed or dipped as a post-molding process), or impregnated (premixed during the material's fluid-resinous state prior to molding), with various agents effective in freshening and combating diseases of the teeth and gums. The well known and popular mint and flouride solutions are easily applied and presented to the user as dry-coatings, quickly activated by the saliva, for proximal release upon tooth surfaces. Fluoride dispensed upon the tooth enamel helps seal-up the enamel tubes, ultimately making the teeth stronger and more resistant to the acids produced by dental bacterial-plaque, food, and sweets. This new flossing material has shown to be very convenient in disbursing coated chemicals such as fluoride, or an antimicrobial such as chlorahexadine-gluonate, known in the marketplace as PERIDEX®(Colgate-Palmolive Corp.) or PERIGUARD®(Procter & Gambel Corp.); which act to destroy bacterial-cells. It is also quite useful with antibiotics such as TETRACYCLINE®(or it's equivalent), to stop the reproduction of bacterial-cells in areas of the teeth prone to decay;—which are frequently shown not very effectively reached by fluoride-toothpaste or fluoride-rinses.

When using the floss-loop embodiment of the invention for dislodging and removing adherent matter which may develop into dental plaque, the preferred continuous circular embodiment hereof makes it easier to mechanically disrupt the dental bacterial plaque colonies, thereby effectively inhibiting production of acids causing dental disease. The prime cause of dental decay and gum disease (gingivitis and periodontal diseases) being dental plaque. This plaque removing device makes the manual action of the hands easier to manipulate between the teeth. It is not necessary to wrap the floss about the fingers of the opposite hands, in order to obtain a positive grip for flossing, mere grasping of the loop between forefinger and thumb of both hands to pull it taut creates a comfortable stance by which to perform the action and manipulation of the floss-loop.

This floss-loop may be employed subgingivally, that is—under the gumline, and if pre-coated with fluoride will effectively seal the area of the tooth not protected by sufficient enamel, but covered with the tooth structure cementum (which is even more susceptible to decay than tooth-enamel). Sealing the tooth's cenemtum tubules with fluoride actually makes that region of the tooth more resistant to the sort of decay seen extensively among older adults (which may have exposed-roots, caused by age, toothbrush abrasion, or gum disease). The fluoride dispensed upon the root surface also helps decrease root sensitivity to hot & cold, and to acidic foods; as well as to a certain degree, destroying bacteria which causes dental disease.

The antiseptic disbursed on the tooth surface of the floss-loop or floss-tape will facilitate destroying the bacteria on the teeth. Since presently about 87% of the population over the age of thirty-five have some form of periodontal-disease, this problem is important to recognize as epidemic. Years ago, people feared one of the processes of aging was to loose one's teeth from dreaded gum-disease, and would as a matter of course obtain a nice set of dentures. However, we now know that by destroying the bacteria, one can create a real impact upon prevention, preservation, treatment, and cure of gum-disease. Since 80% of the gum-diseased areas in the mouth are lodged between the teeth, it is imperative to floss daily. The dispersion of chemical and antibiotic therapy is proven to immobilize and even eliminate the gum-disease bacteria; and will, by virtue of the invention hereof, further treat this dreadful human epidemic.

We know today that the adverse bacterial-plaque forms upon the teeth about twice a day, and is the responsible source for the production of acids that cause dental-decay and gum-disease. Most of the areas effected by these diseases are between the teeth, which is why it is so important to use dental-floss daily. Studies show that most people do not floss, owing that it is time consuming, tedious, fustrating, often difficult to insert interstitially owing to thickness of the flossing device; and, many people are simply not proficient at the manual-dexterity technique involved in the flossing process, because they have become discouraged from lack of a suitably designed flossing device. The exceptional new dental-hygiene invention hereof, is intended to introduce an important new preventative tool for a modern society.

III.) DESCRIPTION OF THE PREFERRED EMBODIMENT DRAWINGS

The foregoing and still other objects of this invention will become fully apparent, along with various advantages and features of novelty residing in the present embodiments, from study of the following description of the variant generic species embodiments and study of the ensuing description of these embodiments. Wherein indicia of reference are shown to match related matter stated in the text, as well as the claims section annexed hereto; and accordingly, a better understanding of the invention and the variant uses is intended, by reference to the drawings, which are considered as primarily exemplary and not to be therefore construed as restrictive in nature; wherein:

IV.) ITEMIZED NOMENCLATURE REFERENCES

10—basic floss-loop
11,11"—thin edge (lower/upper)
12/12"—elastomeric progression reference-lines
13/13"—typical sidewall-surface (outside-face/inside-face)
14—longitudinal-axis
15/15"—unused loose portions
16/16"—dangling-ends
17/17'/17"—left hand (different sequences)
18/18'/18"—right hand (different sequences)
19—gum-tissue sulcus
20—linear-tape
21/21"—interstitial region
22/22"—typical abutting teeth

V.) DETAILED DESCRIPTION OF THE PREFERRED EMBODIMENTS

Figure 1:
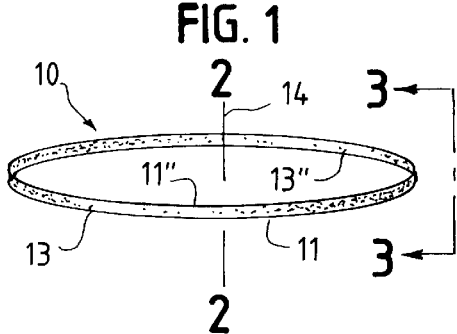
FIG. 1, is a pictorial-view representing the floss-loop embodiment in it's basic relaxed form.
Figure 4:
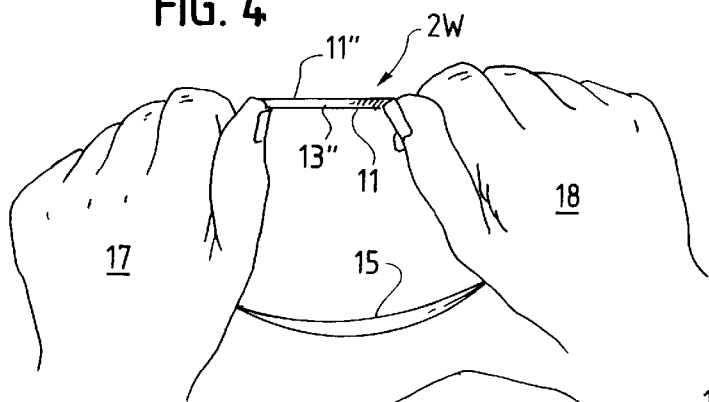
FIG. 4, is a pictorial-view showing the relationship of human hands holding the special flossing-loop device.
Figure 5:
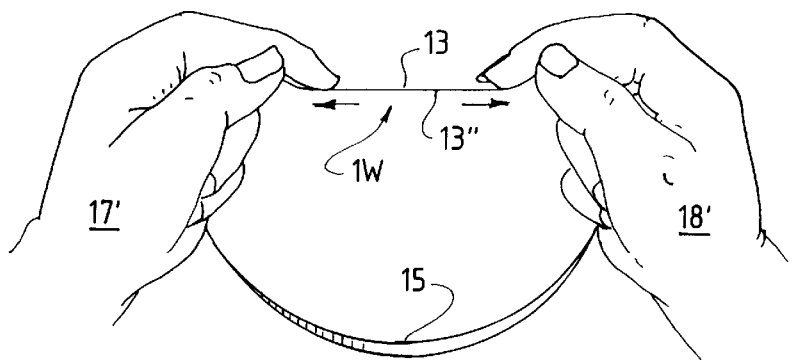
FIG. 5, is an alternate manner of holding thereof.

Initial reference is given by way of FIG. 1, wherein is exhibited the basic preferred continuous floss-loop configuration 10 which is prepared for operation by merely grasping the loop in the opposed fingers and thumb of both left 17 and right 18 hands, then stretching the loop, leaving 1½–3 inches suspended in-between the fingers per FIGS. 4&5, while the unused portion merely dangles 15 freely from the finger-tips.

To floss one's lower-teeth for example, one need only direct flossing-edge 11 downward interstitially by holding the two index-fingers aside of the band's broad sidewall surface 13; while alternately, flosing-edge 11" is likewise effective upwardly within the upper-teeth interstitials. The index-finger can also be used to hold the floss on the inside of the teeth, while the other index-finger holds the floss-loop to the outside of the teeth.

Figure 2:
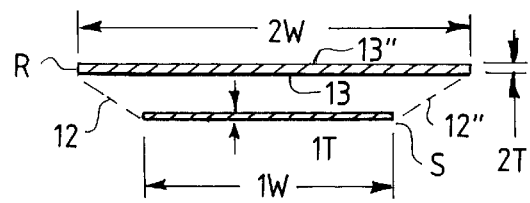
FIG. 2, is a 10×-enlarged cross-sectional view thereof, taken through plane 2:2 of FIG. 1, including an alternate comparative physical representation.

Study of FIG. 2 reveals how the elongated rectangular (approx. 1:8 thickness-to-width ratio) cross-section of the floss-loop (and floss-tape) can be stretched-"S" taut (2×-elongation) to an approximate exceptional near film-like nominal 0.0080-inch(0.203 mm) guage thickness for easier interstitial insertion between tight contacts of the teeth, whereupon the floss-loop is substantially relaxed-"R" at an approximate nominal 0.0128–inch(0.325 mm, or generally less than 1/64th") guage thickness to attain optimal interstitial thickness reexpansion and vertical-surface 13/13" exposure While cleaning the teeth. The unusual physical dynamics of this variable-guage stretching action is indicated in FIG. 2, wherein the natural substantially relaxed-mode "R" width condition "2W" and commensurate thickness condition "2T", is shown in contrast to the alternate almost film-like stretched-mode condition "1W" and "1T". That this is a finitely variable-ratio of width and thickness(guage) is indicated via broken reference-lines 12/12", and is a direct function of the physical tension exerted per examples of FIGS. 4&5 usage. Note that while FIG. 4 clearly shows (obliquely, between the fingers and thumbs) the floss-loop's inside sidewall surface 13" and the upper-edge 11", FIGS. 5&6 portray only the tensed upper-edge thickness 11", therefore the material appears visually thinner in the latter illustrations.

Figure 3:
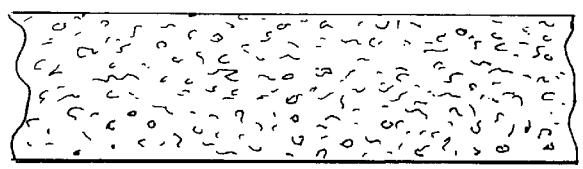
FIG. 3, is a full side/elevation-view taken along plane 3:3 of FIG. 1, serving to reveal preferred surface texture character.

There remain subtle, however vital other differences which are to become herein more evident and understood as important improvements. For example, greatly enlarged FIG. 3 shows the textured surface 13, characterized as having an apparent translucent planar sheen when held per FIGS. 4&5, the sheen being broken only by a regular variegated pock-marked like texture of a random nature. The individual floss-loops 10 of FIG. 1 are uniquely produced from urethane-resin via extrusion-molding process; then when cooled, radially-sliced to the desired 2W(shown) or 3W width relative to longitudinal-axis 14. This novel process enables a much more durable continuous-loop 10, eliminating the problematical production or user requirement of having to physically attach (via overlapping) the ends of a tape in order to make a type of loop configuration (yet, which tends to break). The specifically preferred tough urethane translucent polymer material is being produced in clear, pale-blue, pale-pink, and pale-green (mint), impregnated color hues; serving for marketing purposes, to signify to the user the different therapeutic and medicinal coatings being offered for their choosing.

Figure 6:
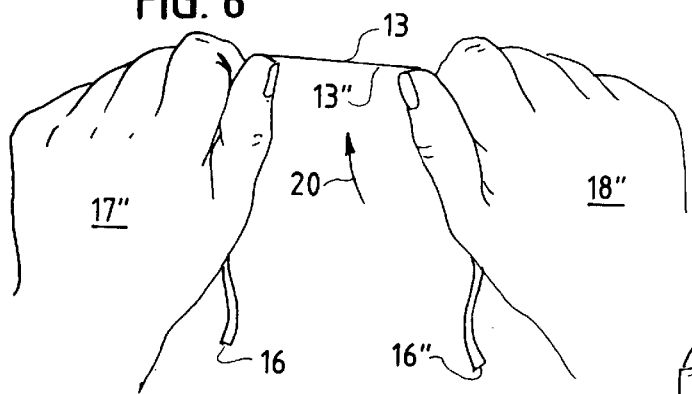
FIG. 6, shows a holding position similar to FIG. 4, but with an alternate flossing-tape embodiment.

Reference to FIG. 6 reveals an alternate (non-continuous) linear floss-tape type embodiment 20 having separate opposite ends 16/16', is furnished in individual user strips of sufficient length as to be held in the opposed fingers of both hands, or otherwise supplied from a roll; and otherwise features the very same physical properties per FIGS. 2&3. Generally however, the floss-tape embodiment is not considered as precise and convenient to manipulate in the fingers, in as much as it tends to slip out of one's grasp more easily than the more preferred continuous-loop 10.

Figure 7:
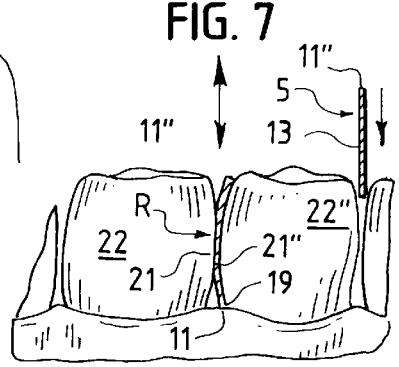
FIG. 7, shows a side-elevation of some lower abutting teeth.

In final FIG. 7, is exemplified a typical environ of abutting teeth, wherein the flossing material is shown both stretched thin "S" initially at right just prior to downward insertion, and then at left in relaxed "R" condition within interstitial sidewalls 21/21" of respective teeth 22 and 22". Note here how the lower-edge 11 of the subject flossing medium is shown impinging upon the sulcus 19 of the supporting gum-tissue, which it does not excessively abrade owing to it's own particular supple pliancy. Once inserted interstitially, the user exerts a vigorous linear oscillating motion per FIG. 5 ref.arrows, first biasing the floss material toward tooth surface 21, then toward tooth surface 21".

Thus, it is readily understood how the preferred and generic-variant embodiments of this invention contemplate performing functions in a novel way not heretofore available nor realized. It is implicit that the utility of the foregoing adaptations of this invention are not necessarily dependent upon any prevailing invention patent; and, while the present invention has been well described hereinbefore by way of certain illustrated embodiments, it is to be expected that various changes, alterations, rearrangements, and obvious modifications may be resorted to by those skilled in the art to which it relates, without substantially departing from the implied spirit and scope of the instant invention. Therefore, the invention has been disclosed herein by way of example, and not as imposed limitation, while the appended Claims set out the scope of the invention sought, and are to be construed as broadly as the terminology therein employed permits, reckoning that the invention verily comprehends every use of which it is susceptible. Accordingly, the embodiments of the invention in which an exclusive property or proprietary privilege is claimed, are defined as follows.

What is claimed of proprietary inventive origin is:

1. A dental floss device, comprising:

an elongated member of stretchable elastomeric polymer material, the member forming an endless uninterrupted loop and being of uniform rectangular cross-section along its length in an unstretched, relaxed condition, the member having a relaxed thickness to width ratio of 1:8;

the member being stretchable between the relaxed condition and a maximum possible extended condition, the thickness of the member being reduced by approximately half between the unstretched and maximum stretched condition;

the member having a first pair of opposite faces adapted to engage teeth of a user, each opposite face of said first pair having a textured cleaning surface extending over the entire area of the respective face, said textured cleaning surface comprising indentations in the polymer material; and the member having a second pair of opposite faces, each opposite face of said second pair being substantially smooth and flat.

2. The device as claimed in claim 1, wherein the textured surfaces are pock-marked.

3. The device as claimed in claim 1, wherein material thickness in the unstretched condition is approximately 0.0128 inches (0.325 mm) and the material thickness in a stretched condition is approximately 0.0080 inches (0.203 mm).

4. A dental flossing device, comprising:

a polyurethane based polymer stretchable material formed to an endless uninterrupted loop having a rectangular cross-section having a minimal relaxed 1:8 thickness to width ratio;

the material having a normal thickness gauge of approximately 0.325 mm when in a relaxed condition and approximately 0.200 mm when in a manually stretched condition;

the formed material having a first pair of opposite side faces adapted to engage teeth of a user, each opposite side face of said first pair being a random textured cleaning surface with a variegated, lightly pock-marked finish; and the formed material having a second pair of opposite side faces, each opposite side face of said second pair being substantially smooth and flat.

5. The device as claimed in claim 4, wherein the material is formed into an endless loop of substantially uniform cross-section around the entire circumference of the loop.

6. The device as claimed in claim 4, wherein the material is translucent and impregnated with a color impregnation.

7. The device as claimed in claim 4, wherein the material is pre-treated with a chemical fluoride agent.

8. The device as claimed in claim 4, wherein the material is treated with antimicrobial chorahexadine-gluconate.

9. The device as claimed in claim 4, wherein the material is treated with an antibiotic substance.

10. The device as claimed in claim 4, wherein the material is coated with a dry-coating agent having a flavor.

11. A method of making a dental floss device, comprising:

extruding a cylindrical tube from a urethane resin, said cylindrical tube having a circumference, a thickness of approximately 0.325 mm and a longitudinal axis;

cooling said cylindrical tube until said tube hardens; and slicing said cylindrical tube substantially perpendicular to said longitudinal axis to create loops, said loops having a width approximately 8 times said thickness.

12. The method as claimed in claim 11, further comprising texturing an internal surface and an external surface of said cylindrical tube prior to said slicing.

13. The method as claimed in claim 12, wherein said texturing provides a variegated, lightly pock-marked finish.

14. The method as claimed in claim 11, further comprising impregnating said cylindrical tube with a color impregnation.

15. The method as claimed in claim 11, further comprising pre-treating said urethane resin with a chemical fluoride agent.

16. The method as claimed in claim 11, further comprising treating said urethane resin with antimicrobial chorahexadine-gluconate.

17. The method as claimed in claim 11, further comprising treating said urethane resin with an antibiotic substance.

18. The method as claimed in claim 11, further comprising coating said cylindrical tube with a dry-coating agent having a flavor.

* * * * *